US011992442B2

(12) United States Patent
Ito

(10) Patent No.: US 11,992,442 B2
(45) Date of Patent: May 28, 2024

(54) SURGICAL HEAD FIXATION APPARATUS

(71) Applicant: MIZUHO CORPORATION, Tokyo (JP)

(72) Inventor: Shinya Ito, Niigata-ken (JP)

(73) Assignee: MIZUHO CORPORATION, Tokyo (JP)

( * ) Notice: Subject to any disclaimer, the term of this patent is extended or adjusted under 35 U.S.C. 154(b) by 1139 days.

(21) Appl. No.: 16/337,228

(22) PCT Filed: Sep. 28, 2016

(86) PCT No.: PCT/JP2016/078599
§ 371 (c)(1),
(2) Date: Mar. 27, 2019

(87) PCT Pub. No.: WO2018/061104
PCT Pub. Date: Apr. 5, 2018

(65) Prior Publication Data
US 2019/0298597 A1 Oct. 3, 2019

(51) Int. Cl.
*A61G 13/00* (2006.01)
*A61B 90/14* (2016.01)
(Continued)

(52) U.S. Cl.
CPC ............ *A61G 13/121* (2013.01); *A61B 90/14* (2016.02); *A61G 13/101* (2013.01); *A61G 13/1295* (2013.01)

(58) Field of Classification Search
CPC ... A61B 2090/571; A61B 90/14; A61B 90/25; A61B 90/35; A61B 90/16; A61B 90/11;
(Continued)

(56) References Cited

U.S. PATENT DOCUMENTS 4,547,092 A * 10/1985 Vetter ...................... F16B 2/04
248/229.11
5,582,379 A * 12/1996 Keselman .............. A61G 13/12
5/624
(Continued)

FOREIGN PATENT DOCUMENTS

DE 11 2007 002 226 4/2017
JP 01-126958 5/1989
(Continued)

OTHER PUBLICATIONS

International Search Report in PCT/JP2016/078599 dated Dec. 20, 2016.
(Continued)

Primary Examiner — Adam Baker
(74) Attorney, Agent, or Firm — DLA Piper LLP (US)

(57) ABSTRACT

A surgical head fixation apparatus according to the present invention includes: a head holder for holding the head of a patient; an articulated link unit which supports the head holder and which is composed of a plurality of link sections; and a support base unit which has a support shaft supporting the articulated link unit and which is to be detachably mounted to an operating table on which the patient is to be placed. The articulated link unit includes at least one link-shaped clamping operation unit which constitutes a link section(s) and which has an operating lever. The link-shaped clamping operation unit has, as pivot axes, at least a first axis and a second axis which are parallel to the support shaft, and a third axis extending in the axial direction of the link-shaped clamping operation unit. The state of the link-shaped clamping operation unit can be switched, through the operation of the operating lever, between three modes: a clamped state in which a pivoting movement on the first axis and a pivoting movement on the second axis are simultaneously locked, an unclamped state in which a pivoting movement
(Continued)

on the third axis becomes possible, and a ready-to-clamp state which is an intermediate state between the unclamped state and the clamped state and in which the pivoting movement on the third axis is locked, while the pivoting movement on the first axis and the pivoting movement on the second axis are unlocked.

12 Claims, 12 Drawing Sheets

(51) Int. Cl.
*A61G 13/10* (2006.01)
*A61G 13/12* (2006.01)

(58) Field of Classification Search
CPC ......... A61B 90/17; A61B 90/30; A61B 90/50; A61B 90/57; A61G 13/101; A61G 13/121; A61G 7/1084; A61G 7/072; A61G 7/0506
USPC ........................................................ 128/845
See application file for complete search history.

(56) References Cited

U.S. PATENT DOCUMENTS

| | | | |
|---|---|---|---|
| 5,897,087 A * | 4/1999 | Farley | A61B 90/50 248/316.2 |
| 7,314,331 B1 * | 1/2008 | Koros | A61B 90/50 403/DIG. 4 |
| 7,552,492 B2 | 6/2009 | Rolfes et al. | |
| 7,628,561 B2 | 12/2009 | McFadden | |
| 9,753,483 B1 * | 9/2017 | Thomas | G05G 5/06 |
| 2006/0185092 A1 | 8/2006 | McFadden | |
| 2008/0072381 A1 * | 3/2008 | Rolfes | A61B 90/14 5/637 |

FOREIGN PATENT DOCUMENTS

| | | |
|---|---|---|
| JP | 11-004837 | 1/1999 |
| JP | 2008-194144 | 8/2008 |
| WO | WO 2008/036720 | 3/2008 |

OTHER PUBLICATIONS

International Preliminary Report on Patentability and Written Opinion in PCT/JP2016/078599 issued Dec. 20, 2016.

* cited by examiner

SURGICAL HEAD FIXATION APPARATUS

CROSS REFERENCE TO RELATED APPLICATIONS

This application is a U.S. National Stage Application of International Application No. PCT/JP2016/078599 filed Sep. 28, 2016. The entirety of all the above-listed applications are incorporated herein by reference.

TECHNICAL FIELD

Embodiments of the present invention relate to a surgical head fixation apparatus, and more particularly to a surgical head fixation apparatus which is used to fix the head of a patient to an operating table e.g. in brain surgery.

BACKGROUND ART

When performing brain surgery, it is necessary to fix the head of a patient in a position adapted for the surgery after placing the patient on an operating table. This is because in brain surgery, a surgical blade or the like is used directly in the brain of a patient under a microscope. if the patient's head moves suddenly, the surgeon may become clumsy and could cause a serious medical accident, such as damage a portion irrelevant to a diseased site.

Therefore, it is conventional practice to provide an operating table with a head fixation apparatus for fixing the head of a patient so that the heat will not move. Examples of prior art documents that describe such a head fixation apparatus include Japanese Patent Laid-Open Publications Nos. H11-4837 and 2008-194144.

It is important in brain surgery to ensure a good operative field for a surgery site. The position and the direction of a patient's head in which it is fixed upon surgery may vary depending on the operative procedure, the diseased site, etc.

In order to be able to respond to various situations, some head fixation apparatus use an articulated link mechanism to support a head, and have a high degree of freedom for fixing position and direction. The use of such an articulated link mechanism makes it possible to fix the head of a patient in the optimum position and direction upon surgery.

SUMMARY OF THE INVENTION

However, in such a conventional head fixation apparatus, each joint of an articulated link mechanism needs to be unclamped before moving the link. Thereafter, upon determination of the position and direction of the head of a patient, each joint must be re-clamped. The conventional apparatus thus necessitates a complicated and time-consuming operation to finally fix the head of a patient.

Further, it sometimes becomes difficult with the progress of surgery to ensure a good visual field in the initial fixed position and direction of the head of a patient. In such a case, it is necessary to operate the conventional head fixation apparatus to move the position and/or the direction of the head slightly during surgery. Also in that case, it is difficult for the conventional apparatus to quickly fix the head.

The present invention has been made in view of the above problems in the prior art. It is therefore an object of the present invention to provide a surgical head fixation apparatus which can fix the head of a patient in a desired position and a desired direction, and can perform clamping/unclamping of an articulated link mechanism quickly in a simple manner.

In order to achieve the object, the present invention provides a surgical head fixation apparatus comprising: a head holder for holding the head of a patient; an articulated link unit which supports the head holder and which is composed of a plurality of link sections; and a support base unit which has a support shaft supporting the articulated link unit and which is to be detachably mounted to an operating table on which the patient is to be placed, wherein the articulated link unit includes at least one link-shaped clamping operation unit which constitutes a link section(s) and which has an operating lever, wherein the link-shaped clamping operation unit has, as pivot axes, at least a first axis and a second axis which are parallel to the support shaft, and a third axis extending in the axial direction of the link-shaped clamping operation unit, and wherein the state of the link-shaped clamping operation unit can be switched, through the operation of the operating lever, between three modes: a clamped state in which a pivoting movement on the first axis and a pivoting movement on the second axis are simultaneously locked, an unclamped state in which a pivoting movement on the third axis becomes possible, and a ready-to-clamp state which is an intermediate state between the unclamped state and the clamped state and in which the pivoting movement on the third axis is locked, while the pivoting movement on the first axis and the pivoting movement on the second axis are unlocked.

DESCRIPTION OF EMBODIMENTS

An embodiment of a surgical head fixation apparatus according to the present invention will now be described with reference to the attached drawings.

Figure 1:
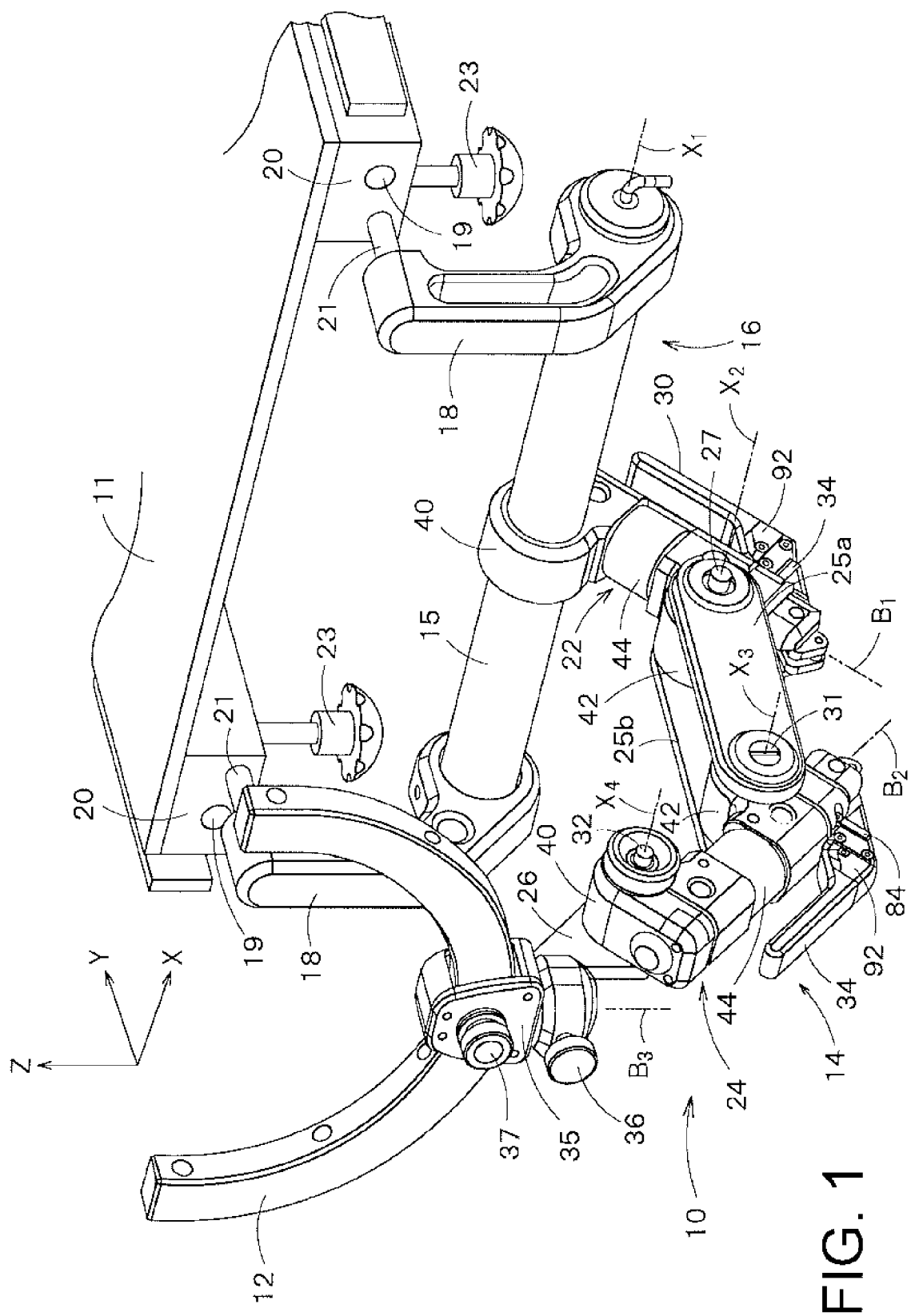
FIG. 1 is an overall perspective view of a surgical head fixation apparatus according to an embodiment of the present invention.

FIG. 1 is an overall perspective view of a surgical head fixation apparatus according to an embodiment of the present invention. At the outset, the surgical head fixation apparatus will be outlined with reference to FIG. 1.

In FIG. 1, reference numeral 10 denotes the surgical head fixation apparatus. Reference numeral 11 denotes an operating table on which a patient is to be placed.

The surgical head fixation apparatus 10 of this embodiment comprises, as main components, a head holder 12 to be mounted to the head of a patient so as to hold the head, an articulated link unit 14 that supports the head holder 12, and a support base unit 16 which has a support shaft 15 supporting the articulated link unit 14, and which is to be mounted to the operating table 11.

The following axes are defined to clarify the movement directions of components of the articulated link unit 14. X-axis is an axis whose direction is parallel to the width direction of the operating table 11, and Y-axis is an axis perpendicular to the X-axis on a horizontal plane. Z-axis is a vertical axis.

The articulated link unit 14 of this embodiment has X1-axis, X2-axis, X3-axis and X4-axis, which are parallel to the X-axis, as the axes of pivoting movements of link sections. The X1-axis functions also as a linear movement axis. The articulated link unit 14 also has B1-axis, B2-axis and B3-axis, which are perpendicular to the X-axis, as the axes of pivoting movements of link sections.

Detailed construction of the surgical head fixation apparatus 10 will now be described.

The support base unit 16 will be described first.

Brackets 18 are mounted on both ends of the support shaft 15 that supports the articulated link unit 14. Fixing blocks 20, each having a hole 19 and a leg 23, are provided in the two corners of the operating table 11. The support shaft 15 is supported horizontally at the end of the operating table 11 by inserting a pin 21 of each bracket 18 into the hole 19.

The articulated link unit 14 comprises the following link sections: The articulated link unit 14 comprises, as main link sections, a first link-shaped clamping operation unit 22, a second link-shaped clamping operation unit 24, intermediate link members 25a, 25b that link the units 22, 24, and a front-end link 26.

Referring to FIG. 1, a base end portion of the first link-shaped clamping operation unit 22 is pivotably and axially movably mounted on the support shaft 15. Thus, the first link-shaped clamping operation unit 22 is pivotable on the X1-axis and movable in the X1-axis direction.

One-side ends of the intermediate link members 25a, 25b are connected via a connecting shaft 27 to the front end of the first link-shaped clamping operation unit 22. The intermediate link members 25a, 25b are pivotable on the X2-axis which is parallel to the X1-axis. The first link-shaped clamping operation unit 22 is configured to be pivotable on the B1-axis which is the central axis.

Thus, in the first link-shaped clamping operation unit 22, the pivoting movement on the X1-axis and the movement in the X1-axis direction, the pivoting movement on the X2-axis, and the pivoting movement on the B1-axis are possible. The first link-shaped clamping operation unit 22 is provided with a clamping mechanism which, by operating an operating lever 30, can perform a clamping operation to simultaneously fix positions of components on the axes and an unclamping operation to simultaneously unclamp the components, as will be described below.

One end of the second link-shaped clamping operation unit 24 is pivotably connected via a connecting shaft 31 to the front ends of the intermediate link members 25a, 25b, so that the second link-shaped clamping operation unit 24 is pivotable on the X3-axis. The other end of the second link-shaped clamping operation unit 24 is connected via a connecting shaft 32 to the front-end link 26. The front-end link 26 is pivotable on the X4-axis. The second link-shaped clamping operation unit 24 is configured to be pivotable on the B2-axis which is the central axis.

Thus, in the second link-shaped clamping operation unit 24, the pivoting movement on the X3-axis, the pivoting movement on the X4-axis, and the pivoting movement on the B2-axis are possible. As with the first link-shaped clamping operation unit 22, the second link-shaped clamping operation unit 24 is provided with a clamping mechanism which, by operating an operating lever 34, can perform a clamping operation to simultaneously fix positions of the axes and an unclamping operation to release the clamped positions, as will be described below. As with the first link-shaped clamping operation unit 22, the second link-shaped clamping operation unit 24 is provided with a clamping mechanism which, by operating an operating lever 34, can perform a clamping operation to simultaneously fix positions of components on the axes and an unclamping operation to simultaneously unclamp the components.

A holder 35, by which the head holder 12 is held, is coupled to the front-end link 26. The semicircular head holder 12 is secured to the holder 35 by tightening a bolt 37. The holder 35 incorporates a shaft (not shown) for rotating the holder 35. The shaft is fixed by tightening a bolt 36. Thus, the head holder 12 can pivot on the B3-axis which is perpendicular to the X4-axis, and can be fixed e.g. with a bolt.

Figure 2:
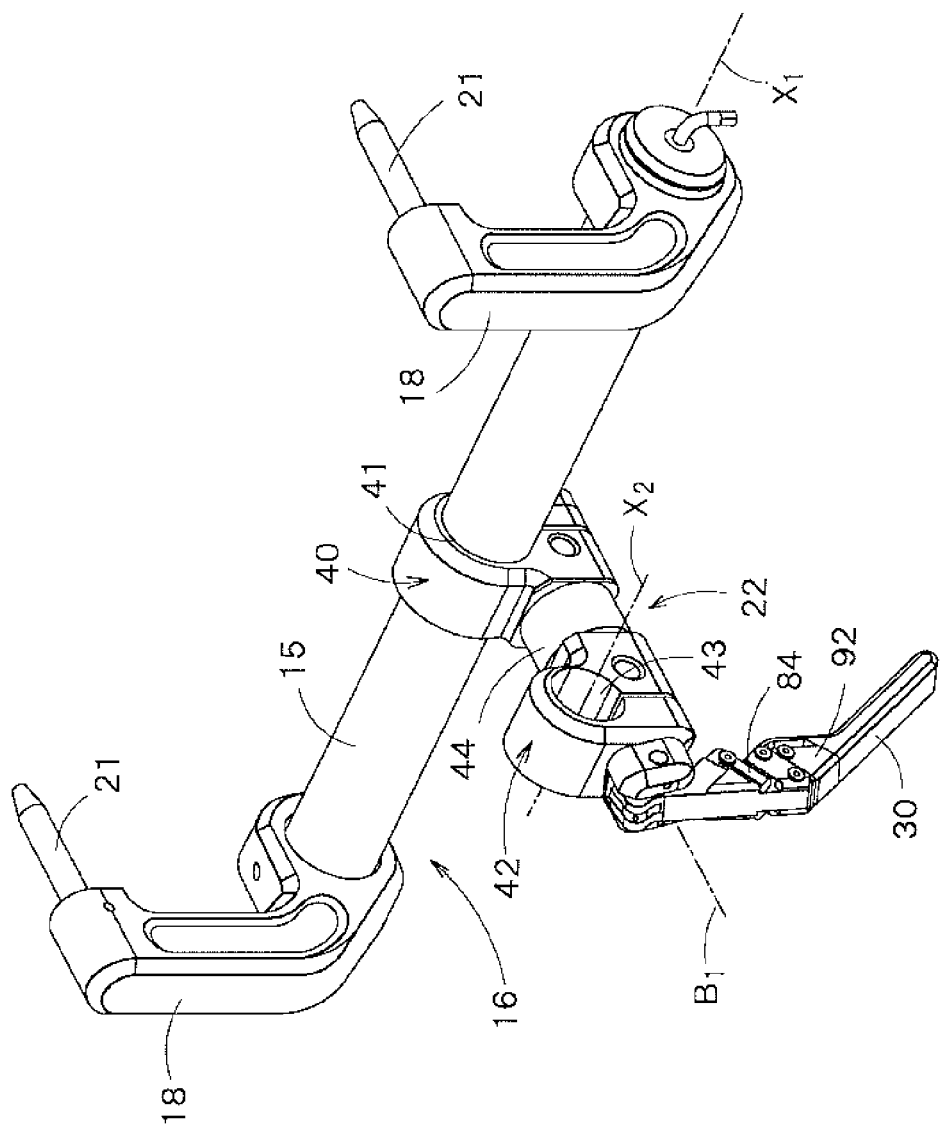
FIG. 2 is a perspective view of a first link-shaped clamping operation unit mounted to a support shaft.

FIG. 2 is a diagram showing the first link-shaped clamping operation unit 22 mounted to the support shaft 15. The second link-shaped clamping operation unit 24 has the same construction as the first link-shaped clamping operation unit 22; therefore, the construction of the first link-shaped clamping operation unit 22 will be hereinafter described in greater detail.

The first link-shaped clamping operation unit 22 mainly comprises a first joint portion 40 having a shaft hole 41, a second joint portion 42 having a shaft hole 43, an intermediate barrel portion 44 having a built-in clamping mechanism, and the operating lever 30 for the clamping mechanism.

As shown in FIG. 2, the support shaft 15 is fitted in the shaft hole 41 of the first joint portion 40 so that the entire first link-shaped clamping operation unit 22 can pivot on the support shaft 15 (on the X1-axis) and can move in the axial direction (X1-axis direction) of the support shaft 15.

Though not shown in FIG. 2, the connecting shaft 27 is fitted in the shaft hole 43 of the second joint portion 42, and the intermediate link members 25a, 25b are connected via the connecting shaft 27 to the second joint portion 42, as shown in FIG. 1. The intermediate link members 25a, 25b are pivotable on the axis (X2-axis) of the connecting shaft 27.

The second joint portion 42 is pivotable on the axis (B1-axis) of the intermediate barrel portion 44 relative to the first joint portion 40.

The operating lever 30 is used to perform an unclamping operation to enable the pivoting movements on the respective axes (X1-axis, X2-axis, B1-axis) and the linear movement in the X1-axis direction, and a clamping operation to fix the positions of components after such movements.

The clamping mechanism of the first link-shaped clamping operation unit 22 will now be described with reference to FIGS. 3 through 5.

By operating the operating lever 30, the state of the first link-shaped clamping operation unit 22 can be switched between three modes: a clamped state, a ready-to-clamp state, and an unclamped state.

Figure 3A:
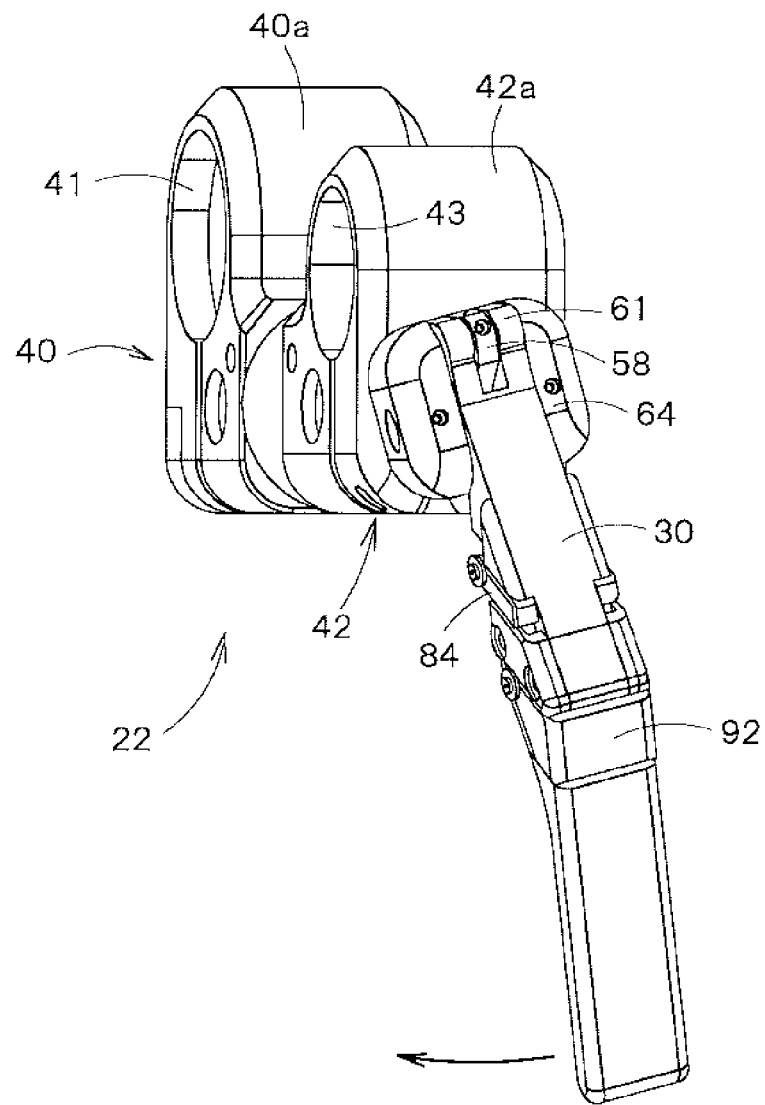
FIGS. 3A through 3C are diagrams showing the first link-shaped clamping operation unit in an unclamped state, FIG. 3A being a perspective view illustrating the position of an operating lever 30, FIG. 3B being a vertical cross-sectional view, and FIG. 3C being a cross-sectional view taken along the line A-A of FIG. 3B.
Figure 3B:
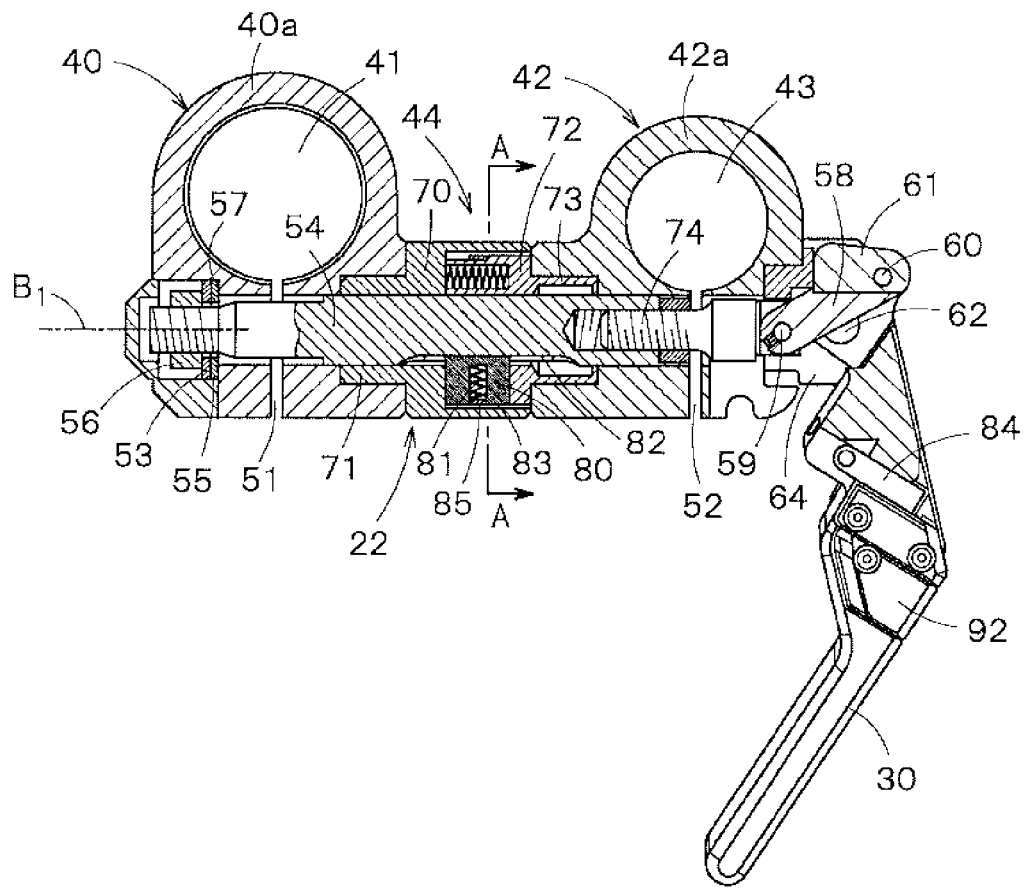
Figure 3C:
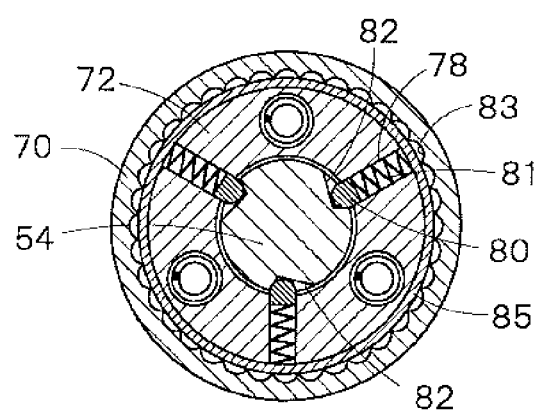

FIGS. 3A through 3C are diagrams showing the first link-shaped clamping operation unit 22 in the unclamped state. The unclamped state herein refers to a state in which all the pivoting movements on the axes (X1-axis, X2-axis, B1-axis) and the linear movement in the X1-axis direction are possible.

Figure 4A:
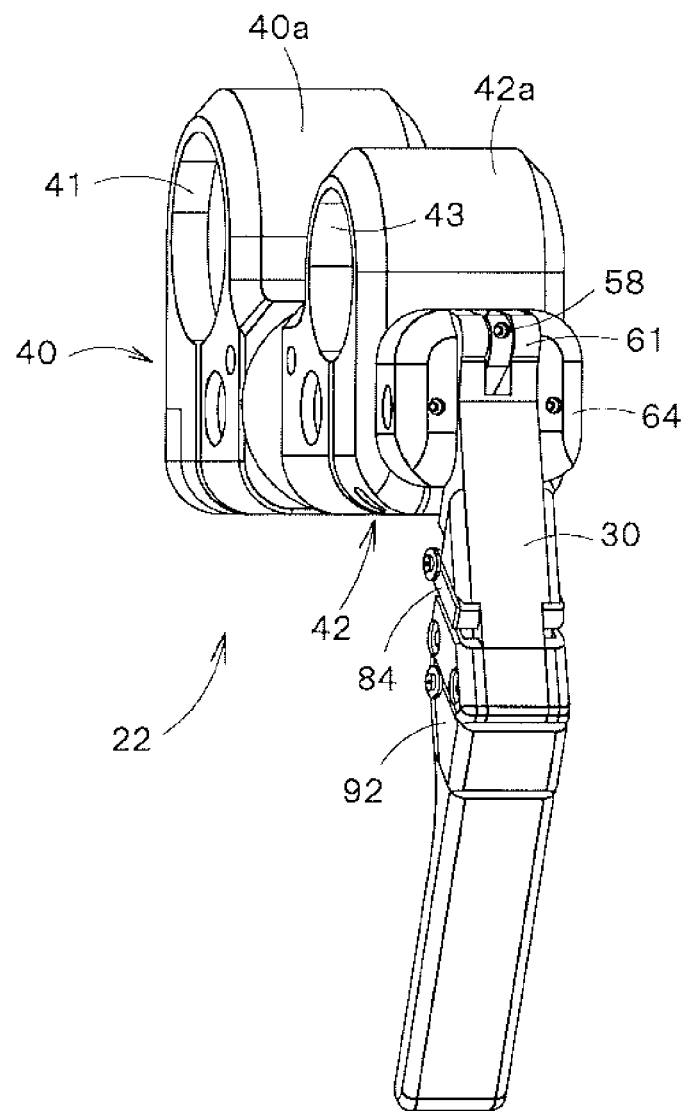
FIGS. 4A through 4D are diagrams showing the first link-shaped clamping operation unit in a ready-to-clamp state, FIG. 4A being a perspective view illustrating the position of the operating lever 30, FIG. 4B being a vertical cross-sectional view, FIG. 4C being a cross-sectional view taken along the line A-A of FIG. 4B, and FIG. 4D being a perspective view of a clamping mechanism which clamps a pivoting movement on B1-axis.
Figure 4B:
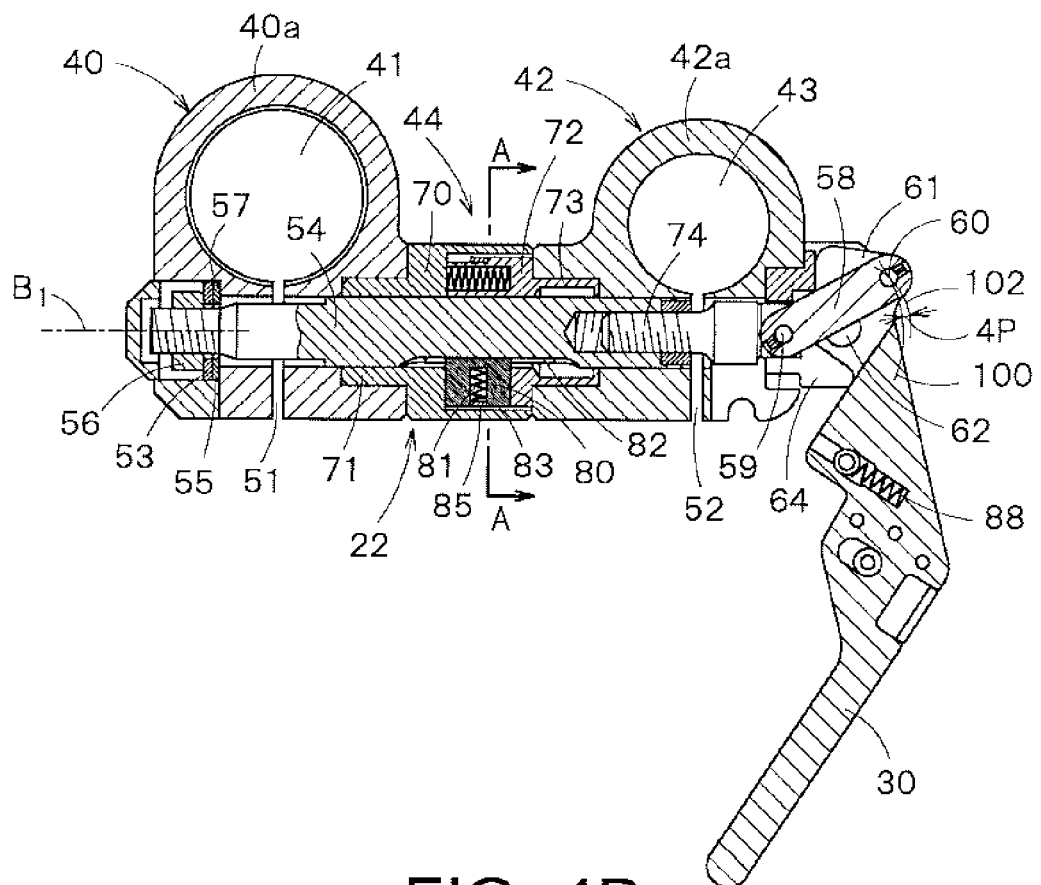
Figure 4C:
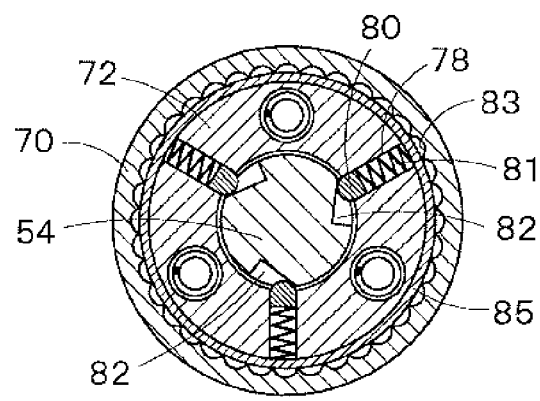
Figure 4D:
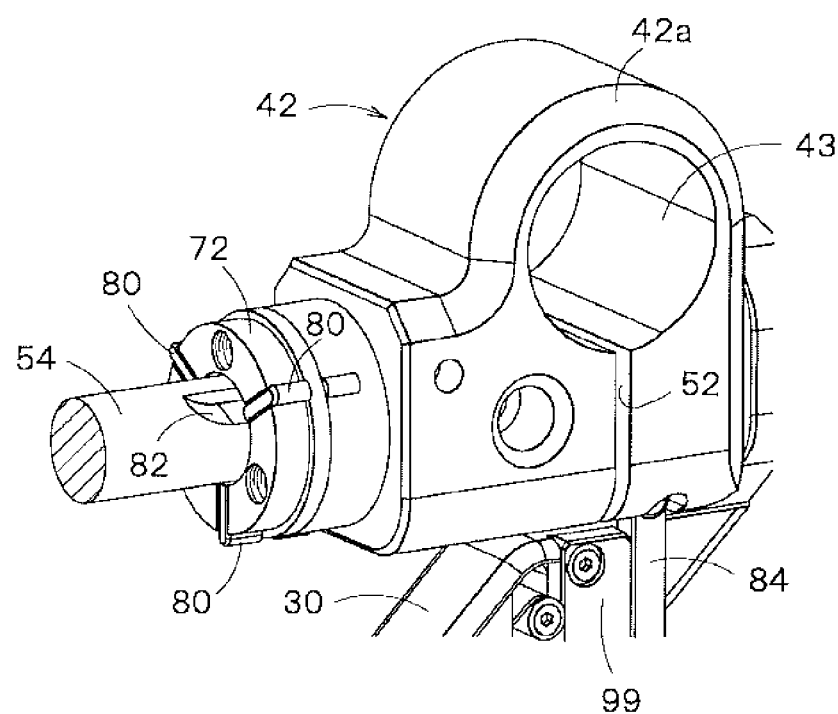

FIGS. 4A through 4D are diagrams showing the first link-shaped clamping operation unit 22 in the ready-to-clamp state. FIG. 4A is a perspective view illustrating the position of the operating lever 30, FIG. 4B is a vertical cross-sectional view, FIG. 4C is a cross-sectional view taken along the line A-A of FIG. 4B, and FIG. 4D is a perspective view of a clamping mechanism which clamps the pivoting movement on the B1-axis. The ready-to-clamp state herein refers to a state in which only the pivoting movement of the second joint portion 42 on the B1-axis is locked.

Figure 5A:
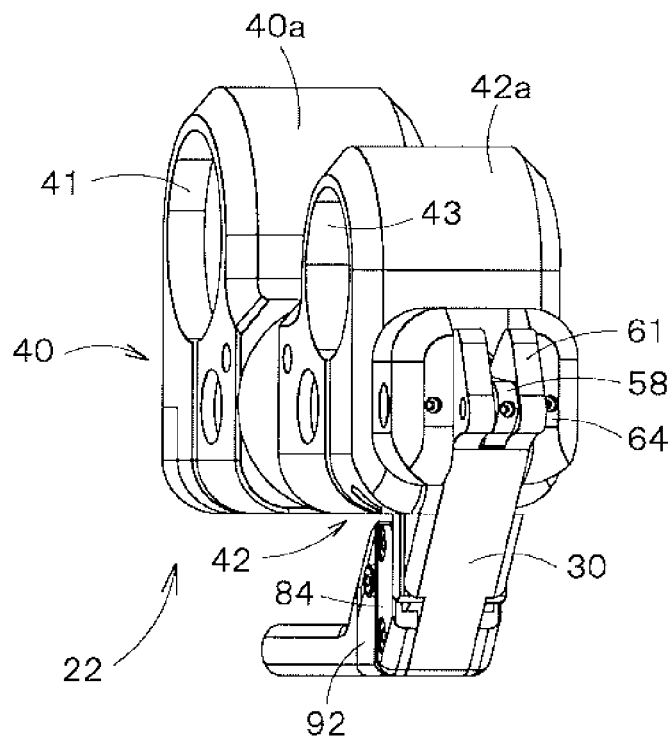
FIGS. 5A and 5B are diagrams showing the first link-shaped clamping operation unit in a clamped state, FIG. 5A being a perspective view illustrating the position of the operating lever 30, and FIG. 5B being a vertical cross-sectional view.
Figure 5B:
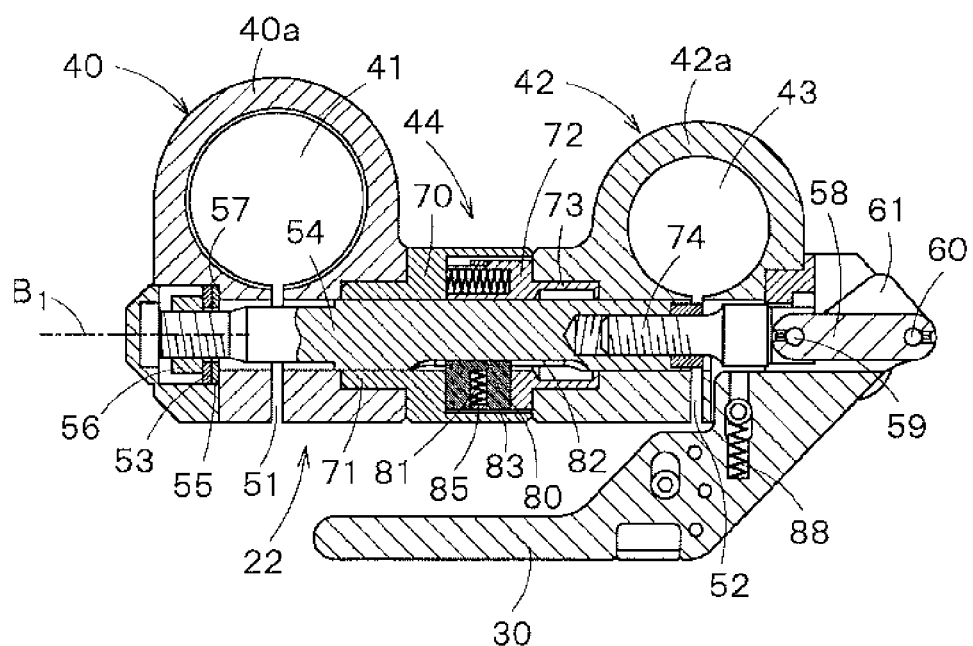

FIGS. 5A and 5B are diagrams showing the first link-shaped clamping operation unit 22 in the clamped state. FIG. 5A is a perspective view illustrating the position of the operating lever 30, and FIG. 5B is a vertical cross-sectional view. The clamped state herein refers to a state in which all the pivoting movements on the axes (X1-axis, X2-axis, B1-axis) and the linear movement in the X1-axis direction are locked.

In the first link-shaped clamping operation unit 22, the first joint portion 40 has a C-shape in which a cylindrical portion 40a, which forms the shaft hole 41, and a slit 51 are formed. Similarly, the second joint portion 42 has a C-shape in which a cylindrical portion 42a, which forms the shaft hole 43, and a slit 52 are formed.

The first link-shaped clamping operation unit 22 has, in its interior, a pull-in shaft 54 that axially penetrates the unit 22. By pulling the pull-in shaft 54 with the operating lever 30, the cylindrical portions 40a, 42a are deformed to thereby narrow the slits 51, 52, whereby the first joint portion 40 and the second joint portion 42 can be clamped.

A nut-receiving washer 53 and a locking ring 55 are mounted via a nut 56 to the front end of the pull-in shaft 54. The locking ring 55 is in engagement with a stepped portion 57 formed in the first joint portion 40. Thus, the front end of the pull-in shaft 54 is fixed at a position on the outer side of the slit 51 (on the side of the front end of the first link-shaped clamping operation unit 22).

The base end of the pull-in shaft 54 projects beyond the slit 52 via a connecting member 74 which, in turn, is connected via a crank 58 to the operating lever 30.

One end of the crank 58 is pivotably coupled via a pin 59 to the connecting member 74, while the other end of the crank 58 is coupled via a pin 60 to a bifurcated connector 61 provided at the base end of the operating lever 30. The base end of the crank 58 is mounted to a block 64, which is integral with the second joint portion 42, pivotably on a shaft 62. The pins 59, 60 and the shaft 62, in their unclamping positions, lie at the vertices of a triangle, and the pin 59 and the shaft 62 lie on the axis of the pull-in shaft 54.

When the operating lever 30 is pivoted from the position shown in FIG. 4(B) to the position shown in FIG. 5(B), the pull-in shaft 54 is pulled by the operating lever 30, whereby the slits 51, 52 are narrowed, and the first joint portion 40 and the second joint portion 42 can be clamped.

On the other hand, the intermediate barrel portion 44 of the first link-shaped clamping operation unit 22 has the following clamping mechanism for fixing the second joint portion 42 so that it will not pivot on the axis (B1-axis) relative to the first joint portion 40.

Referring to FIG. 3B, the intermediate barrel portion 44 includes an outer cylindrical portion 70, an inner cylindrical portion 72, and the pull-in shaft 54. The outer cylindrical portion 70 has a joint 71 that joins with the first joint portion 40, while the inner cylindrical portion 72 has a joint 73 that joins with the second joint portion 42. The pull-in shaft 54 penetrates the inner cylindrical portion 72 and the outer cylindrical portion 70 coaxially.

As shown in FIG. 3C, a plurality of grooves 78 which are symmetrical with respect to the axis, are formed in the inner cylindrical portion 72 such that they radially penetrate the inner cylindrical portion 72. A clamp plate 80 is inserted into each groove 78.

A plurality of cam grooves 82 are formed in the periphery of the pull-in shaft 54 at positions symmetrical with respect to the axis. Each cam groove 82 has a bottom surface which is inclined in the circumferential direction. Each clamp plate 80 is pressed by a spring 81 against each cam groove 82. 85 denotes a spring retainer ring.

The base end of the pull-in shaft 54 is connected to the operating lever 30 via the connecting member 74. The pull-in shaft 54 is configured to rotate when the operating lever 30 is turned in the arrowed direction shown in FIG. 3A, and the clamp plates 80 are forced radially outward by the cam grooves 82 of the pull-in shaft 54.

FIG. 3C illustrates the rotational position of the pull-in shaft 54 in an unclamped position. The front ends of the clamp plates 80 lie on the same level as the outer peripheral surface of the inner cylindrical portion 72. A large number of axially-extending grooves 83 are formed at a predetermined pitch in the inner peripheral surface of the outer cylindrical portion 70. The front ends of the clamp plates 80 can engage the grooves 83.

FIG. 4C illustrates the rotational position of the pull-in shaft 54 in a clamped position.

When the operating lever 30 is turned from the position shown in FIG. 3A to the position shown in FIG. 4A, the pull-in shaft 54 rotates, and forces the clamp plates 80 outward and brings their front ends into engagement with the grooves 83. FIG. 4D illustrates the clamp plates 80 which have been forced outward. In this manner, the outer cylindrical portion 70 and the first joint portion 40 can be clamped so that they will not turn. The engagement between the clamp plates 80 and the grooves 83 is maintained in the subsequent clamped state.

In such a ready-to-clamp state, the first joint portion 40 and the second joint portion 42 are not in a fully clamped state. By pivoting the operating lever 30 from the position shown in FIG. 4(B) to the position shown in FIG. 5(B), the first joint portion 40 and the second joint portion 42 can be clamped as follows.

In FIG. 4B, the curve 100 indicates a trajectory in which the pin 60 moves when the crank 58 pivots on the pin 59. The curve 102 indicates a trajectory in which the pin 60 moves when the operating lever 30 pivots on the shaft 62. Thus, since the center of pivoting movement of the operating lever 30 is offset from the center of pivoting movement of the crank 58, when the crank 58 is pivoted to a position where the crank 58 is aligned with the pull-in shaft 54, the pull-in shaft 54 will be pulled in by a pull-in distance ΔP. On the other hand, since the tail end of the pull-in shaft 54 is in engagement with the stepped portion 57 via the locking ring 55 and therefore is immovable, the force that pulls in the pull-in shaft 54 narrows the slits 51, 52 and deforms the cylindrical portions 40a, 42a of the first joint portion 40 and the second joint portion 42 such that their diameters decrease.

As shown in FIG. 5B, the first joint portion 40 is clamped to the support shaft 15 so that it does not move relative to the support shaft 15, while the second joint portion 42 is clamped to the connecting shaft 27.

Figure 6A:
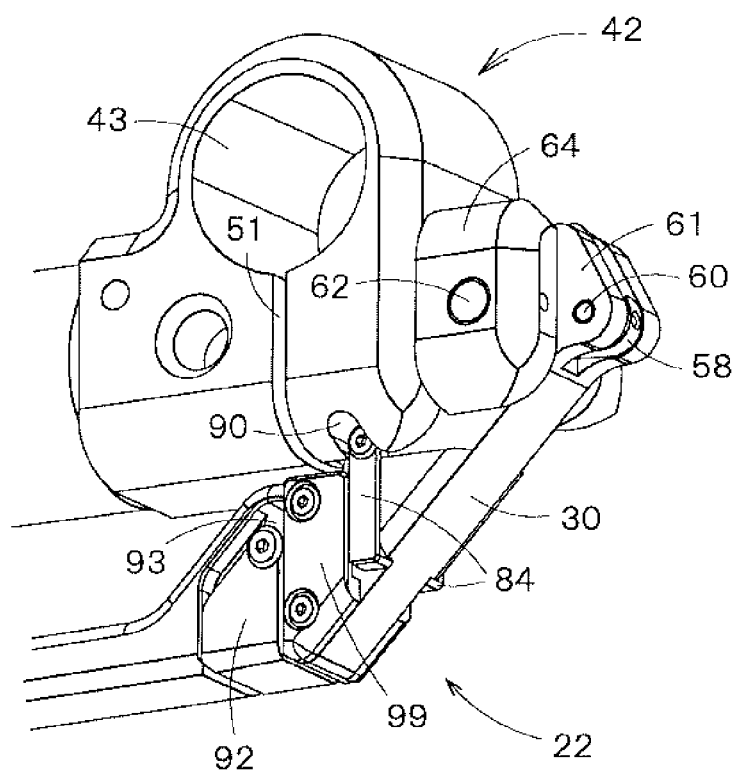
FIGS. 6A and 6B are diagrams showing slide locks provided in the operating lever, FIG. 6A illustrating the state of the operating lever 30 when it is locked by the slide locks 84, and FIG. 6B illustrating the operating lever 30 in an unlocked state.
Figure 6B:
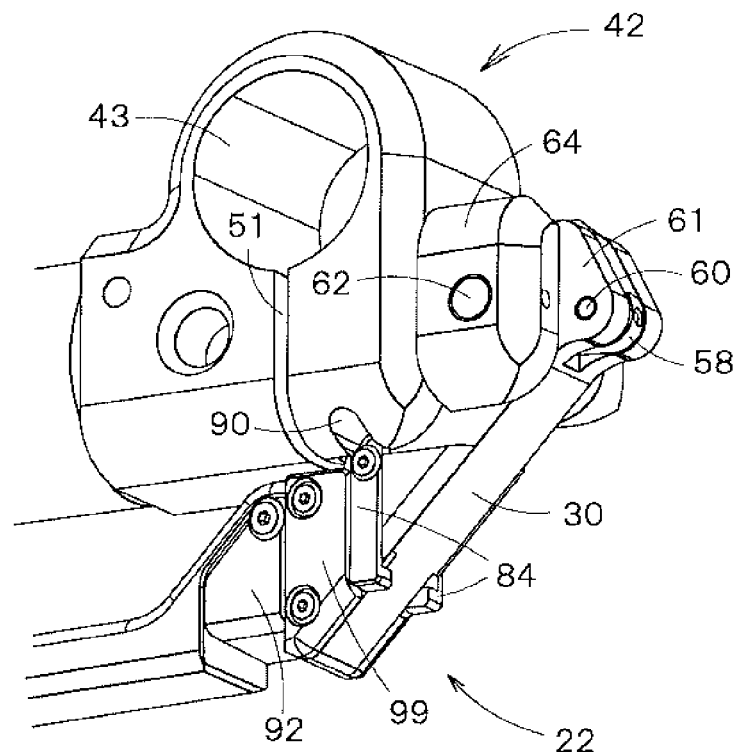
Figure 7:
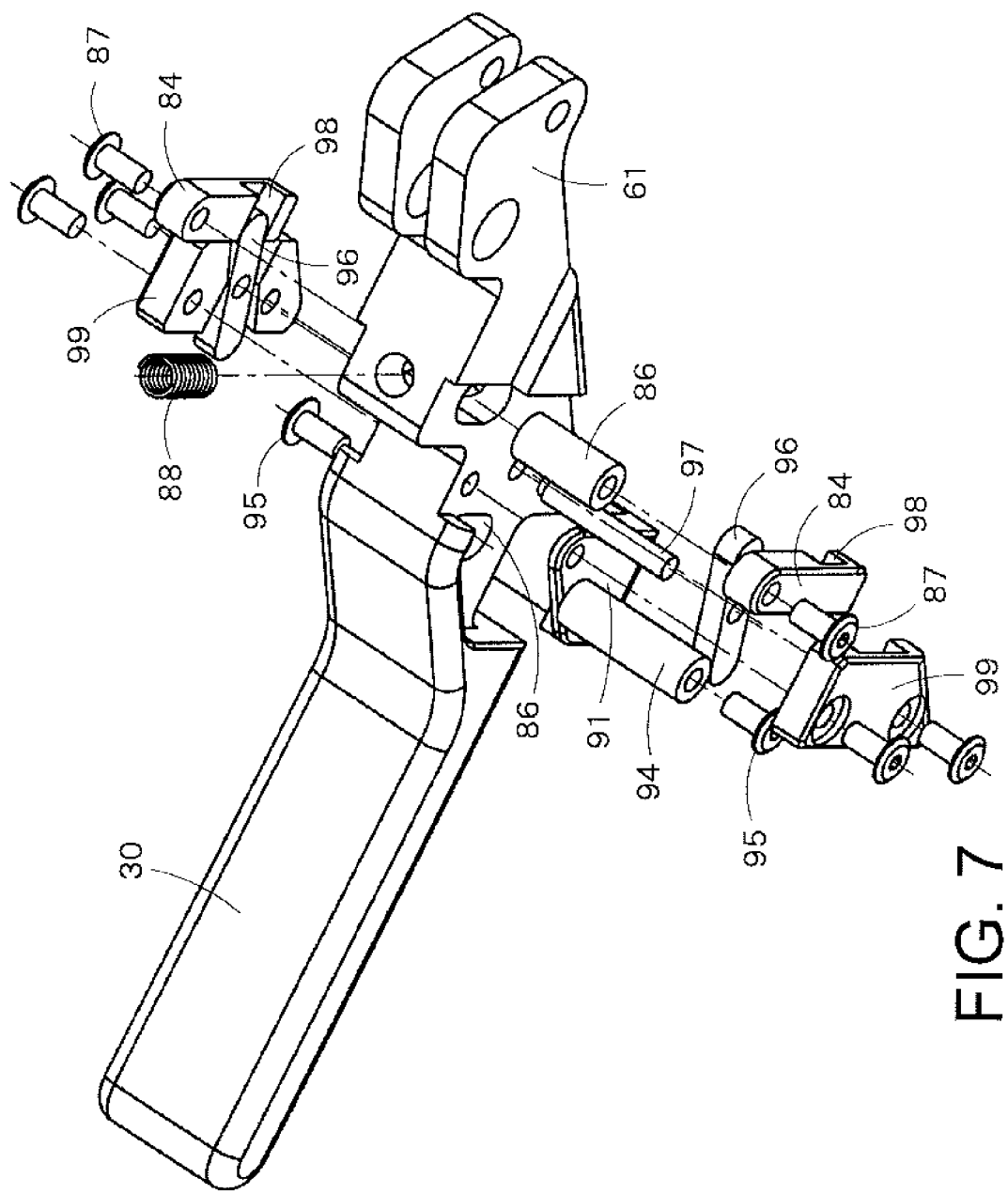
FIG. 7 is an exploded view of a locking/unlocking mechanism including the slide locks 84.

In order to lock/unlock the operating lever 30 in such a clamping position, the operating lever 30 is provided with slide locks 84 as shown in FIGS. 6 and 7. FIG. 6A illustrates the state of the operating lever 30 when it is locked by the slide locks 84, and FIG. 6B illustrates the operating lever 30 in an unlocked state. FIG. 7 is an exploded view of a locking/unlocking mechanism including the slide locks 84.

The slide locks 84 are provided in a pair on both sides of the operating lever 30 slidably thereon. A spring retainer member 86 is housed in the interior of the base end of the operating lever 30, and the slide locks 84 are secured with screws 87 to both ends of the spring retainer member 86. Further, a coil spring 88 is housed in the interior of the base end of the operating lever 30, and the slide locks 84 are continually biased in a locking direction by the elastic force of the coil spring 88. The second joint portion 42 has cutout grooves 90 which engage the front ends of the slide locks 84 when the operating lever 30 is closed in the clamping position.

The operating lever 30 of this embodiment is provided with the following pair of release buttons 92 to unlock the operating lever 30 locked with the slide locks 84. A cylindrical piece 94, which is inserted into a guide hole 93 formed in the operating lever 30, is secured with screws 95, 95 to ends of the release buttons 92. The release buttons 92 are movable with the guide hole 93 as a guide.

The release buttons 92 and the slide locks 84 are connected by a pair of interlocking cranks 96 provided on both sides of the operating lever 30. The interlocking cranks 96 are swingably supported by a crank shaft 97, and are parts to interlock the slide locks 84 with the release buttons 92. One end of each interlocking crank 96 engages a groove 98 formed in each slide lock 84, while the other end of the interlocking crank 96 contacts the release button 92. In FIG. 7, 99 denotes a cover member that covers each interlocking crank 96.

Figure 8:
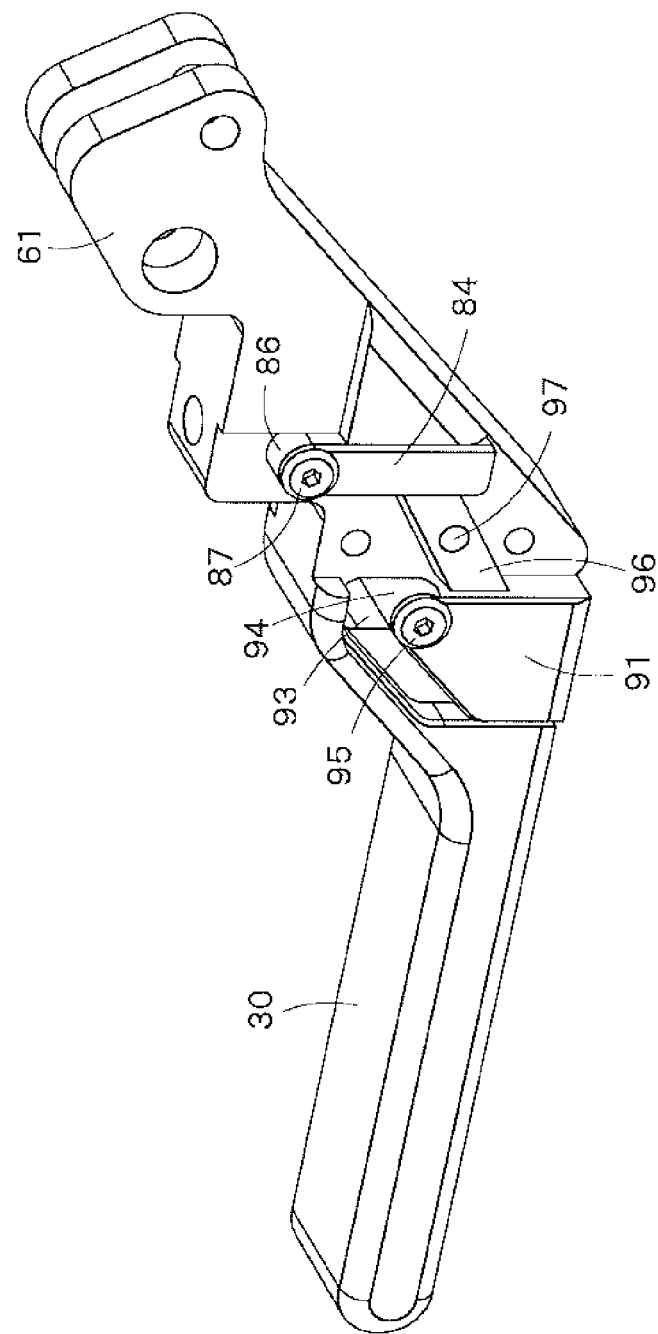
FIG. 8 is a perspective view of the slide locks.

FIG. 8 is a diagram illustrating how the release buttons 92 and the slide locks 84 are interlocked by the interlocking cranks 96. When the release buttons 92 are pressed in the arrowed direction shown in FIG. 8, the slide locks 84 move backward from their locking positions, thereby unlocking the operating lever 30.

Figure 9A:
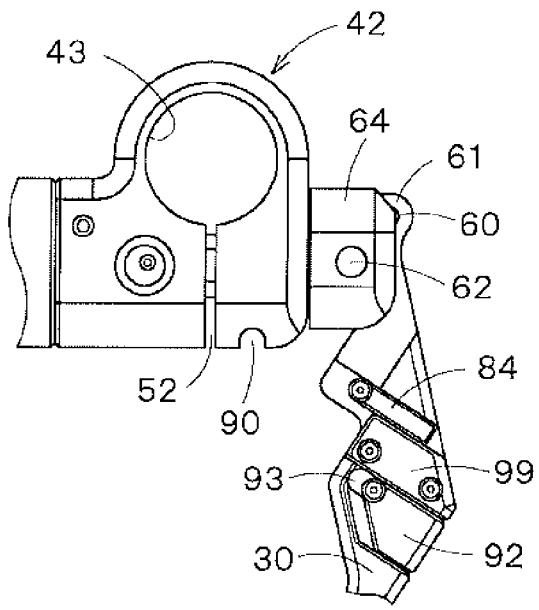
FIGS. 9A through 9C are diagrams illustrating how the slide locks move when the operating lever pivots.
Figure 9B:
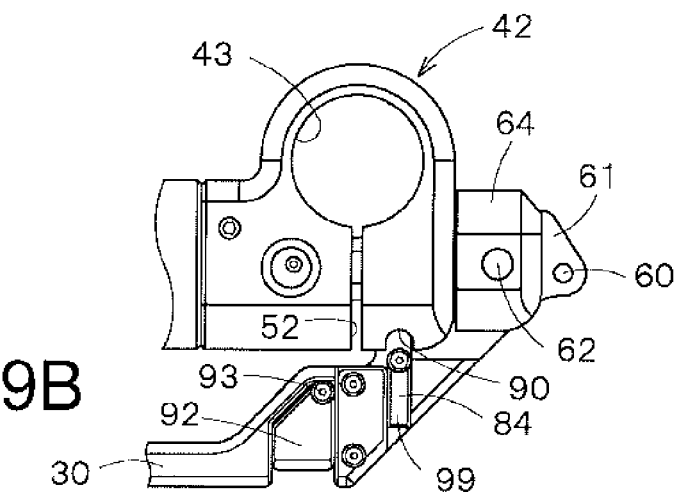
Figure 9C:
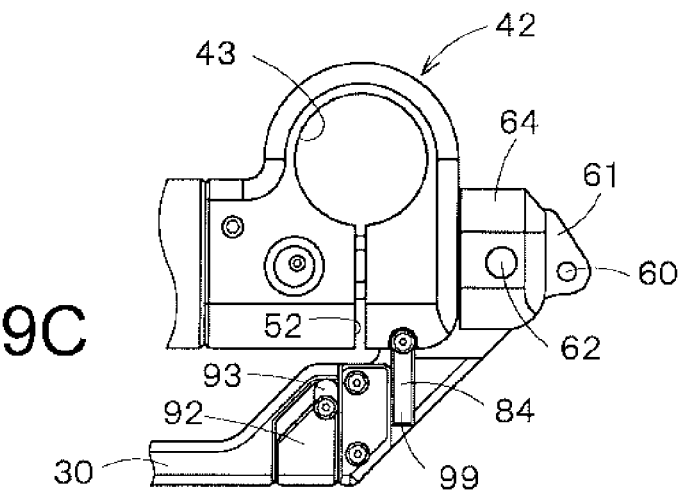

FIGS. 9A through 9C are diagrams illustrating how the slide locks 84 move when the operating lever 30 pivots.

As shown in FIGS. 9A through 9C, when the operating lever 30 pivots in the closing direction and reaches the fully-clamping position (FIG. 9C), the front ends of the slide locks 84 engage the cutout grooves 90. At the same time, the first joint portion 40 and the second joint portion 42 become the above-described clamped states. The slide locks 84 are held by the elastic force of the coil spring 88 so that they will not move out of the cutout grooves 90. Thus, the operating lever 30 is locked so that it will not open. In this manner, the operating lever 30 is locked simultaneously with completion of the clamping operation. The operating lever 30 can be unlocked by pressing the release buttons 92 to pull down the slide locks 84, thereby forcing the slide locks 84 out of the cutout grooves 90.

The first joint portion 40 and the second joint portion 42 can be unclamped simply by pivoting the operating lever 30 in the opening direction after unlocking the operating lever 30.

When the operating lever 30 is pivoted from the clamping position shown in FIG. 5B to the ready-to-clamp position shown in FIG. 4B, the pull-in force decreases and no pull-in force acts on the pull-in shaft 54 in the ready-to-clamp position, and therefore the slits 51, 52 become wider, and the cylindrical portions 40a, 42a of the first joint portion 40 and the second joint portion 42 are restored to their original states by their elastic forces. The first joint portion 40 and the second joint portion 42 are thus unclamped simultaneously.

When the operating lever 30 is slightly turned to the position shown in FIG. 3A, the clamp plates 80 move inward as shown in FIG. 3C, whereby the clamping by the clamp plates 80 is released. Thus, through the simple operations of the operating lever 30, the state of the first link-shaped clamping operation unit 22 can be shifted from the unclamped state to the fully clamped state via the ready-to-clamp state, and vice versa.

As shown in FIG. 1, in the surgical head fixation apparatus 10 of this embodiment, the articulated link unit 14 includes the second link-shaped clamping operation unit 24 in addition to the above-described first link-shaped clamping operation unit 22. Since the second link-shaped clamping operation unit 24 has the same construction as the first link-shaped clamping operation unit 22, the same reference numerals are used for the same components, and a duplicate description thereof is omitted.

The above-described surgical head fixation apparatus according to this embodiment achieves the following effects.

The articulated link unit 14, which supports the head holder 12, comprises, as main link sections of an articulated link mechanism, the first link-shaped clamping operation unit 22 and the second link-shaped clamping operation unit 24 each having a clamping function. The first link-shaped clamping operation unit 22 constitutes a link that enables the pivoting movements on the X1-axis, X2-axis and the B1-axis, and the linear movement in the X1-axis direction. The second link-shaped clamping operation unit 24 constitutes a link that enables the pivoting movements on the X3-axis, X4-axis and the B2-axis.

The many axes of movements can thus be imparted to the articulated link unit 14. The head holder 12 therefore has a high degree of freedom and flexibility of its movement, making it possible to easily move the head holder 12 to a position which is optimum for surgery or treatment of a patient.

Furthermore, the first link-shaped clamping operation unit 22 and the second link-shaped clamping operation unit 24 each can perform clamping on the plurality of axes at a time by the simple operation of pivoting the operating lever 30, 34. This facilitates an operation to finally fix the head of a patient and makes it possible to quickly fix the head holder 12 at an optimum position.

While the present invention has been described with reference to the preferred embodiments in which the two link-shaped clamping operation units are used to construct an articulated link, the present invention is not limited to the embodiments. It is possible to use a single link-shaped clamping operation unit, or three or more link-shaped clamping operation units to construct an articulated link.

The invention claimed is:
1. A surgical head fixation apparatus comprising:
a head holder configured to hold the head of a patient;

an articulated link unit configured to support the head holder and comprising a plurality of link sections and at least one link-shaped clamping operation unit which constitutes at least one of the plurality of link sections, the at least one link-shaped clamping operation unit including:
an operating lever,
a plurality of pivot axes including at least a first axis and a second axis, and a third axis extending in the axial direction of the link-shaped clamping operation unit, and
a third-axis clamping mechanism that is configured to perform clamping on the third axis in response to being mechanically engaged by a movement of the operating lever into a fixed position; and
a support base unit comprising a support shaft parallel to the at least the first axis and the second axis and supporting the articulated link unit and which is configured to be detachably mounted to an operating table on which the patient is to be placed,
wherein a state of the link-shaped clamping operation unit is selectively switchable, through an operation of the operating lever, between a plurality of modes comprising:
a clamped state in which a pivoting movement on the first axis and a pivoting movement on the second axis are simultaneously locked,
an unclamped state in which the pivoting movement on the first axis and the pivoting movement on the second axis are unlocked, and a pivoting movement on the third axis is unlocked, and
a ready-to-clamp state which is an intermediate state between the unclamped state and the clamped state and in which the pivoting movement on the third axis is locked by the third-axis clamping mechanism, while the pivoting movement on the first axis and the pivoting movement on the second axis are unlocked, wherein the ready-to-clamp state is entered by the movement of the operating lever into the fixed position, and
the operating lever is rotatable around a first operation axis and a second operation axis that is unparallel to the first operation axis such that the unclamped state is switched to the ready-to-clamp state by rotating the operating lever around the first operation axis and the ready-to-clamp state is switched to the clamped state by rotating the operating lever around the second operation axis.

2. The surgical head fixation apparatus according to claim 1, wherein the link-shaped clamping operation unit includes:
a first joint portion including a cylindrical portion, whose axis is the first axis, and a slit;
a second joint portion including a cylindrical portion, whose axis is the second axis, and a slit;
an intermediate barrel portion which connects the first joint portion and the second joint portion and which includes a built-in third-axis clamping mechanism that is configured to perform clamping on the third axis;
a pull-in shaft disposed such that it internally extends from the first joint portion to the second joint portion via the intermediate barrel portion; and
the operating lever which is connected to a base end of the pull-in shaft via a lever link mechanism and which is configured to simultaneously narrow the slit of the first joint portion and the slit of the second joint portion, thereby clamping the first joint portion and the second joint portion.

3. The surgical head fixation apparatus according to claim 2, wherein:
the lever link mechanism includes a crank, one end of which is coupled via a first pin to a base end of the pull-in shaft, and the other end of which is coupled via a second pin to a base end of the operating lever, and
in the unclamped state, a shaft which pivotably supports the operating lever lies on the axis of the pull-in shaft, and the shaft, the first pin and the second pin lie at the vertices of a triangle.

4. The surgical head fixation apparatus according to claim 3, wherein the articulated link unit includes at least two link-shaped clamping operation units as link sections.

5. The surgical head fixation apparatus according to claim 2, wherein:
the intermediate barrel portion includes an outer cylindrical portion joined to the first joint portion, an inner cylindrical portion joined to the second joint portion, and a sleeve with cam grooves fitted over the pull-in shaft,
a plurality of clamp plates, which are forced radially outward by the cam grooves when the sleeve rotates, are embedded in the inner cylindrical portion, and
grooves, which engage the front ends of the clamp plates, are formed in the inner peripheral surface of the outer cylindrical portion.

6. The surgical head fixation apparatus according to claim 5, wherein the articulated link unit includes at least two link-shaped clamping operation units as link sections.

7. The surgical head fixation apparatus according to claim 2, wherein the operating lever includes a slide lock mechanism configured to lock and unlock the operating lever in a clamping position.

8. The surgical head fixation apparatus according to claim 7, wherein the slide lock mechanism includes:
a slide lock configured to engage the first joint portion or the second joint portion to lock the operating lever,
a release button configured to unlock the operating lever, and
an interlocking crank configured to interlock the release button and the slide lock.

9. The surgical head fixation apparatus according to claim 8, wherein the articulated link unit includes at least two link-shaped clamping operation units as link sections.

10. The surgical head fixation apparatus according to claim 7, wherein the articulated link unit includes at least two link-shaped clamping operation units as link sections.

11. The surgical head fixation apparatus according to claim 2, wherein the articulated link unit includes at least two link-shaped clamping operation units as link sections.

12. The surgical head fixation apparatus according to claim 1, wherein the articulated link unit includes at least two link-shaped clamping operation units as link sections.

* * * * *